US011168127B1

(12) United States Patent
Mitteness et al.

(10) Patent No.: US 11,168,127 B1
(45) Date of Patent: Nov. 9, 2021

(54) PATHOGEN SPECIFIC AVIAN ANTIBODIES IN THE NEONATAL MAMMAL

(71) Applicant: Camas, Incorporated, Le Center, MN (US)

(72) Inventors: Bradley M. Mitteness, Ghent, MN (US); Connie Phillips, Ankeny, IA (US); Jason Hull, New Ulm, MN (US); Michelle Hawkins, Bloomington, MN (US); Ky McCraken, Mankato, MN (US)

(73) Assignee: CAMAS INCORPORATED, Le Center, MN (US)

( * ) Notice: Subject to any disclaimer, the term of this patent is extended or adjusted under 35 U.S.C. 154(b) by 0 days.

(21) Appl. No.: 15/366,773

(22) Filed: Dec. 1, 2016

Related U.S. Application Data

(60) Provisional application No. 62/261,558, filed on Dec. 1, 2015.

(51) Int. Cl.

| | | |
|---|---|---|
| *A61K 39/42* | (2006.01) | |
| *C07K 16/10* | (2006.01) | |
| *A61K 35/20* | (2006.01) | |
| *A61K 39/395* | (2006.01) | |
| *A61K 9/00* | (2006.01) | |
| *A23K 20/147* | (2016.01) | |
| *A61K 39/00* | (2006.01) | |

(52) U.S. Cl.
CPC ............ *C07K 16/10* (2013.01); *A23K 20/147* (2016.05); *A61K 9/0053* (2013.01); *A61K 35/20* (2013.01); *A61K 39/39575* (2013.01); *A61K 2039/505* (2013.01); *A61K 2039/542* (2013.01); *A61K 2039/545* (2013.01); *A61K 2039/55* (2013.01); *C07K 2317/23* (2013.01); *C07K 2317/76* (2013.01)

(58) Field of Classification Search
None
See application file for complete search history.

(56) References Cited

U.S. PATENT DOCUMENTS

| | | | | |
|---|---|---|---|---|
| 7,241,443 B1 * | 7/2007 | Nash | ...................... | C07K 16/12 424/130.1 |
| 2007/0264264 A1 * | 11/2007 | Evans | .................... | C07K 16/10 424/157.1 |
| 2011/0274701 A1 * | 11/2011 | Mitteness | .............. | C07K 16/02 424/157.1 |
| 2012/0141458 A1 * | 6/2012 | Starzl | ..................... | C07K 16/10 424/130.1 |
| 2013/0183286 A1 * | 7/2013 | Mitteness | .............. | C07K 16/02 424/130.1 |

OTHER PUBLICATIONS

Ikemori et al., "Passive protection of neonatal calves against bovine coronavirus-induced diarrhea by administration of egg yolk or colostrum antibody powder," Veterinary Microbiology 58: 105-111 (1997).*
Saif et al., "Bovine Respiratory Coronavirus," Vet Clin North Am Food Anim Pract 26(2): 349-364 (2010).*
Pelzer et al., "Zoonotic Diseases of Cattle," Communications and Marketing, College of Agriculture and Life Sciences, Virginia Polytechnic Institute and State University (2009) (Year: 2009).*
Munhoz et al., "Avian IgY antibodies: characteristics and applications in immunodiagnostic," Ciencia Rural, Santa Maria, v.44, n.1: 153-160 (Year: 2014).*
Schade et al., "Chicken Egg Yolk Antibodies (IgY-technology): A Review of Progress in Production and Use in Research and Human and Veterinary Medicine," ATLA 33: 129-154 (Year: 2005).*
Sacco et al., "Neonatal calf infection with respiratory syncytial virus: drawing parallels to the disease in human infants," Viruses 4(12: 3731-53 (Year: 2012).*
Dubie et al. "The potential application of avian egg antibodies with emphasis on immunotherapeutic and immunodiagnostic purpose," Advanced Research Journal of Biochemistry and Biotechnology: vol. 1(3): 018-030 (Year: 2014).*
Kirkland et al., "Ruminant Pestivirus Infections," Australia and New Zealand Standard Diagnostic Procedures 1-30 (Year: 2006).*
Kitila et al., "Pathological and Serum Biochemical Study of Liver Fluke Infection in Ruminants Slaughtered at ELFORA Export Abbatoir, Bishoftu, Ethiopia," Global Journal of Medical Research, vol. XIV, Issue XIII, Version 1 (Year: 2014).*
Mehlhorn et al. (eds), "Respiratory Diseases, Ruminants," Encyclopedia of Parasitology, Springer, Berlin, Heidelberg (Year: 2008).*
Rudikoff et al., "Single amino acid substitution altering antigenbinding specificity," Proc Natl Acad Sci USA 79:1979-1983 (Year: 1982).*
Hodgins et al., "Respiratory Viruses and Bacteria in Cattle," In: Brogen KA, Guthmiller JM, editors. Polymicrobial Diseases. Washington (DC): ASM Press; 2002, Chapter 12 (Year: 2002).*
Erhard et al., "Systemic availability of bovine immunoglobulin G and chicken immunoglobulin Y after feeding colostrum and whole egg powder to newborn calves," Arch Tieremahr 50(4): 369-80 (Year: 2007).*
Blezinger S., 2013 "The value of feeding egg antibodies", Progressive Dairyman, www.progressivedairy.com/topics/feed-nutrition/the-value-of-feeding-egg-antibodies.

(Continued)

*Primary Examiner* — M Franco G Salvoza
(74) *Attorney, Agent, or Firm* — Westman, Champlin & Koehler, P.A.; Z. Peter Sawicki; Visala C. Goswitz

(57) ABSTRACT

Compositions are described that include colostrum and/or milk replacer combined with pathogen specific avian antibodies. These pathogen specific avian antibodies include antibodies against pathogens causing infections and disease in the digestive tract as well as outside the digestive tract. Feeding regimens and methods for administering the colostrum and/or milk replacer with the pathogen specific avian antibodies result in the presence of IgY antibodies in the serum of a neonatal animal. The IgY antibody in the serum can neutralize pathogens causing infections outside of the digestive tract.

10 Claims, No Drawings

(56) References Cited

OTHER PUBLICATIONS

Hurty J., 2015 "The use of whole-egg antibodies in dairy production", Progressive Dairyman, www.progressivedairy.com/topics/herd-health/the-use-of-whole-egg-antibodies-in-dairy-production.

* cited by examiner

PATHOGEN SPECIFIC AVIAN ANTIBODIES IN THE NEONATAL MAMMAL

CROSS-REFERENCE TO RELATED APPLICATION

The present application is based on and claims the benefit of U.S. provisional patent application Ser. No. 62/261,558, filed on Dec. 1, 2015, the content of which is hereby incorporated by reference in its entirety.

FIELD

The present description relates to compositions and methods for providing immune protection for neonatal mammals.

BACKGROUND

The mammalian newborn or neonate is born with a naïve or inactive immune system. The first immunity is generally supplied by the colostrum received from the mother. In neonatal calves, for example, the colostrum from the dam (the mother of the calf) provides the first immunity. This colostrum contains immunoglobulins that will provide passive immunity for the newborn mammal until their own innate immunity begins to flourish.

The colostrum contains a number of valuable components to ensure the well-being of the newborn, including immunoglobulins against various microbial entities to which the mother has been exposed. The mother or dam can become exposed to microbial entities via either active disease or vaccination specific to these microbes. Thus, the dam generally has circulating antibodies that become deposited into the first colostral milk (up to 3 milkings post-delivery will contain higher than normal levels of antibodies).

Antibodies start to be concentrated or deposited into the colostrum 10-14 days pre-parturition. This can then reduce the mother's own immune system. The microbes that may be present but controlled within the mother are now more likely to expand and are thus shed immediately after delivery of the newborn(s). Thus, the newborn is exposed to such microbial entities in the birth canal or immediately after delivery.

The mammalian neonate does not receive immunoglobulins during growth in the uterus since the immunoglobulins do not pass the placental barrier. This is true for swine, bovine, human and a number of other mammals. The health and future growth success of the neonate is dependent upon the receipt of the protein, immune cells, and immunoglobulins received from the colostrum. In the event, the young does not receive colostrum or receives very weak colostrum, the level(s) of protein and immunoglobulin become too low to provide protection and/or stimulation of the young's own immune system.

Within the veterinary world, the lack or reduced receipt of such protein and immunoglobulins is known as "Failure of Passive Transfer". It is often a cause of early morbidity and mortality. Current products to enhance or provide immune support are antisera from horse, goat, and adult cow. These are injectable products which can only be given once to the neonate since repeated usage (injections) will cause allergic or anaphylactic shock.

Avian antibodies to neonatal animals have been provided. The avian antibodies are administered over a period of time until the neonatal animal develops its own immunity, i.e. development of the active immune system. The avian antibodies have been used to protect the neonatal animal against infections of the digestive tract since the avian antibodies line the gut of the neonatal animal and were thought not to be absorbed into the bloodstream at any point in the neonatal animal. The amount of avian antibodies to be administered has been variable. Amounts in excess of 280 grams of avian antibodies in the first 3 feedings are disclosed as well as amounts as low as 2-4 grams/day to slowly introduce the avian antibodies to a calf are also taught. The avian antibodies have been administered until the neonatal animals develop their own immune system. Avian antibodies, for example, have been administered for several weeks after birth in order to enhance immune protection in the neonatal animal against pathogenic infections in the digestive tract, i.e. gastric infections.

SUMMARY

In a first aspect, the present description relates to a composition that includes colostrum and/or milk replacer. The composition also includes pathogen specific avian antibodies against at least one pathogen causing an infection in an animal at a site outside of the digestive tract of the animal, wherein the concentration of the pathogen specific avian antibodies in the composition is sufficient for detection of the IgY antibodies derived from the pathogen specific avian antibodies in the serum of an animal. The composition may include between about 5 grams and about 60 grams of the avian antibodies. The composition may include between about 5 grams per quart and about 20 grams per quart of the avian antibodies. The composition may further include pathogen specific avian antibodies against pathogens causing infections in the digestive tract. The pathogen may be selected from bacteria, virus, fungi, parasites and combinations thereof. The pathogen may be bovine coronavirus.

In a another aspect, the present description relates to a neonatal animal feeding regimen including one or more feeding compositions wherein the first feeding compositions comprise colostrum and/or milk replacer; and pathogen specific avian antibodies specific against at least one pathogen causing an infection in the animal at a site outside of the digestive tract of the animal. The amount of the pathogen specific avian antibodies administered in the first feeding composition may be between about 5 grams and about 250 grams and wherein the total amount of the pathogen specific avian antibodies administered in the regimen is less than about 250 grams. The total amount of the pathogen specific avian antibody may be in the first feeding composition. The amount of the pathogen specific avian antibodies in the first feeding composition may be between about 10 grams and about 60 grams. The regimen may further include one or more subsequent feeding compositions after the first feeding composition, wherein the one or more subsequent feeding compositions include pathogen specific avian antibodies, wherein the subsequent feeding compositions are administered within 24 hours of birth. The first feeding composition may include between about 10 grams and about 60 grams of the avian antibodies and the one or more subsequent feeding compositions may include between about 10 grams and about 120 grams of the total avian antibodies, when the subsequent feeding compositions are for administration within 24 hours of birth.

In a further aspect, the present disclosure relates to a method of treating a neonatal animal. The method includes administering a first feeding composition comprising colostrum and/or milk replacer, the first feeding composition further comprising pathogen specific avian antibodies against at least one pathogen causing an infection outside of the digestive tract of the animal, the concentration of the avian antibodies in the composition sufficient to detect the presence of IgY antibodies from the pathogen specific avian antibodies in the serum of the animal. The first feeding composition may include between about 5 grams and about 60 grams of the avian antibodies. All of the mammalian protein in the composition may be derived from fresh colostrum. The pathogens may be bacteria, virus, fungi, parasite and combinations thereof. The method may further include administering one or more subsequent feeding compositions after the first feeding composition, the one or more subsequent feeding compositions comprising pathogen specific avian antibodies, wherein the total amount of avian antibodies administered in the first feeding composition and the one or more subsequent compositions is less than about 250 grams. The feeding compositions may further include pathogen specific avian antibodies against pathogens causing digestive tract infections. The one or more subsequent compositions may be administered to the neonatal animal within 24 hours from birth.

In yet a further aspect, the present disclosure relates to a method of treating a neonatal animal for non-digestive tract infections. The method includes administering a composition comprising colostrum and/or milk replacer, the composition further comprising pathogen specific avian antibodies specific for one or more pathogens in a first feeding to the neonatal animal, the neonatal animal having or being susceptible to a non-digestive tract infection by the one or more pathogens, the amount of the avian antibodies in the composition sufficient to detect the presence of IgY antibodies of the avian antibodies in the serum of the animal. The non-digestive infections may be selected from respiratory infections, naval infections, kidney infections, lung infections and combinations thereof.

In a yet another aspect, the present disclosure relates to a method of treating a neonatal animal with avian antibodies consisting essentially of administering pathogen specific avian antibodies and colostrum and/or milk replacer in a first feeding to the neonatal animal, the avian antibodies specific for one or more pathogens causing non-digestive tract infections, the amount of the avian antibodies in the composition sufficient to detect the presence of IgY antibodies from the avian antibodies in the serum of the animal, wherein the neonatal animal is not administered avian antibodies in subsequent feedings.

DETAILED DESCRIPTION OF ILLUSTRATIVE EMBODIMENTS

The present description relates to feeding compositions for neonatal animals and methods for feeding neonatal animals. The feeding compositions can include colostrum and/or milk replacer. The feeding compositions can also include pathogenic specific avian antibodies combined with colostrum and/or milk replacer wherein the avian antibodies are specific for one or more pathogens. The pathogen specific avian antibodies included in the feeding compositions can include antibodies against at least one pathogen causing an infection in the animal at a site other than the digestive tract of the animal. In exemplary embodiments, the feeding compositions can include pathogenic specific avian antibodies against pathogens that may cause disease in the digestive tract as well as disease in sites outside of the digestive tract.

Preferably, the first feeding composition is administered shortly after birth and includes pathogen specific avian antibodies combined with colostrum and/or milk replacer. One or more subsequent feeding compositions, i.e. feeding compositions administered after the first feeding composition, may also include the pathogen specific avian antibodies combined with colostrum and/or milk replacer. The pathogen specific avian antibodies included in the first feeding composition and optionally, other subsequent feeding compositions administered within about 24 to about 48 hours from birth are directed against pathogens that can infect and cause disease in sites outside of the digestive tract. Preferably, the amount of pathogen specific avian antibodies in these feeding compositions are sufficient and effective for detection of IgY antibodies derived from the avian antibodies in the serum of the neonatal animal. Feeding compositions to be administered to the neonatal animal after about 24-48 hours of birth do not require the inclusion of the pathogen specific avian antibodies directed against pathogens causing infections at non-gastrointestinal sites.

The feeding compositions and methods described herein provide an early enhancement of the colostral protein and immunoglobulins with avian antibodies, especially specific to disease entities which often impair the very young animals, i.e. neonatal animal. The neonatal animal can be infected very soon after delivery and does not have any immunity that can prevent or slow such infections. The neonatal animal is thus very limited in its ability to respond to and block any challenge from microbes during the very early days of its life.

Without being bound by any theory, the IgY antibodies derived from the avian antibodies are thought to provide protection by lining the gut and providing a barrier at the lining of the digestive tract by binding the pathogens resident in the gut. In other words, the IgY antibodies derived from the avian antibodies are thought to be unable to cross the digestive tract barrier. Surprisingly, it has been demonstrated in the present disclosure that avian antibodies administered to neonatal animals after birth can be detected in the serum of the animal. Furthermore, the ability of the avian antibodies to cross the digestive tract barrier is transient. It is thought that the first feeding can stimulate gut closure in the neonatal animal and that the avian antibodies begin losing their ability to cross the digestive tract and into the serum after the first feeding and totally lose the ability to cross the digestive tract within about 24-48 hours.

The present disclosure relates to protection for neonatal animal against pathogens or pathogenic infections occurring in locations in the digestive tract as well as outside of the digestive tract. The pathogen specific avian antibodies included in the feeding compositions can be directed to, for example, pathogenic respiratory tract infections, naval infections, kidney infections and the like. The avian antibodies against pathogens that cause infections in locations other than the digestive tract can be administered within the first 24-48 hours after birth of the neonatal animal and should be administered before closure of the gut, i.e. in the first 24-48 hours after birth. Avian antibodies against pathogens causing digestive tract infections may be administered after 24-48 hours from birth and until the neonatal animal develops its own immunity after birth since these antibodies do not need to cross the digestive tract barrier.

The present methods relate to administering pathogen specific avian antibodies to neonatal animals. One method includes administration of pathogen specific avian antibodies combined with colostrum and/or milk replacer. The pathogen specific avian antibodies against pathogens causing infections at sites other than the digestive tract can be administered in colostrum and/or milk replacer in feedings up to about 24-48 hours after birth. Administration of avian antibodies in the first feedings can enable the IgY derived from the avian antibodies to cross the barrier in the digestive tract and enter the serum of the neonatal animal. The presence of IgY in the serum can protect the neonatal animal from infections that occur in a variety of systems such as respiratory infections, naval infections, kidney infections and the like.

"Neonatal animal" and "neonate" as used herein are interchangeable and relate to an animal from birth to about 28 days. Neonatal animals can be a variety of mammals. The mammals can be ruminants or non-ruminants and include, for example, calves, piglets, horses, sheep, goats, and the like.

"Pathogen specific avian antibodies" as used herein relate to avian antibodies that are specific for a given pathogen(s) or pathogenic components such as pathogen lysates, LPS and the like. These pathogens can include pathogens that cause infections in the digestive tract and/or also pathogens that can cause infections in sites other than the digestive tract, e.g. non-digestive tract infections.

"Distal sites" or "non-gastric sites" or "non-digestive tract sites" as used herein relate to sites other than the digestive tract and can include, for example, respiratory, kidney, lung, liver, naval and the like.

Avian antibodies to early challenges, can be taken up via the "open" gastrointestinal tract when administered orally in the first 24 to 48 hours after birth and can be found in the circulating serum of the neonate for several days following use in the young animal. These circulating IgY antibodies isolated from sera of the neonatal animal can be a neutralizing antibody to early viral disease caused by, for example, a coronavirus. The use of pathogen specific avian antibodies with the first feeding and for several feedings after can provide early and specific immune protection for the neonate as they develop their own innate immune system. Additionally, the use of the avian antibodies provides increased and/or enhanced total protein (TP) to the neonate.

The present description includes pathogen specific avian antibodies in a regimen that can include one or more feeding compositions. "Feeding composition" as used herein includes colostrum and/or milk replacer and is administered orally to the neonatal animal. The feeding composition can further include pathogen specific avian antibodies against one or more pathogens. Preferably, the first feeding composition can include colostrum and/or milk replacer combined with the pathogen specific avian antibodies. More preferably, the first feeding composition includes colostrum combined with the pathogen specific avian antibodies. "First feeding composition" as used herein relates to the first composition administered orally after birth to the neonatal animal. The pathogen specific antibodies are preferably against at least one pathogen that causes an infection in a distal site, e.g. naval, respiratory, kidney and the like. The pathogen specific avian antibodies included in the feeding compositions may be against multiple pathogens. The antibodies in the feeding composition can be against two or more pathogens wherein the combination of pathogens can cause digestive tract infections as well non-digestive tract infections, e.g. at a distal site. Alternatively, the antibodies can be against two or more pathogens that all cause or are capable of causing non-digestive tract infections, e.g. at a distal site.

The colostrum may be from the dam of the neonatal animal. Milk replacer, if used, can be any commercially available milk replacer. Alternatively, the colostrum may be from another dam or a powdered colostrum that is reconstituted. In an exemplary embodiment, the first feeding can be colostrum from the dam and the one or more subsequent feedings can be a milk replacer.

The avian antibodies included in the feeding compositions can be pathogen specific avian antibodies. Pathogen specific antibodies are made by hyper-immunizing hens as described, for example, in U.S. Pat. No. 7,241,443 to Nash et al. and incorporated herein by reference. The avian antibodies can be specific for a variety of pathogens and/or pathogen components. The pathogens can be bacteria, virus, fungi, parasites and the like. Pathogen specific avian antibodies can be against viruses such as Bovine Respiratory Syncytial Virus (BRSV), Bovine coronavirus, Rotavirus, herpes virus, ParaInfluenza 3 (PI3), Adenovirus, Bovine Viral Diarrhea Virus (BVDV), and Infectious Bovine Rhinotracheitis (IBR). Pathogen specific avian antibodies can also be against bacteria such as *Pasteurella multocida, Mannheimia haemolytica, Histophilus somni, Mycoplasma bovis*). Parasitic (lungworm) and fungal (*Aspergillus*) agents. Pathogen specific avian antibodies include antibodies against lysates, LPS components of bacteria and other cellular components. Other suitable pathogen specific avian antibodies may also be combined with the feeding compositions described herein.

Infections from the pathogens may occur in a variety of locations in the neonatal animals and can include, for example, respiratory infections, lung infections, naval infections, kidney infections, joint infections, brain infections and the like. Pathogenic specific avian antibodies can be effective against a variety of diseases such as Bovine Respiratory Disease (BRD). As described herein, the feeding composition may also include pathogen specific avian antibodies against pathogens directed to digestive tract infections in addition to pathogen specific avian antibodies against pathogens directed to non-digestive tract infections.

As described above, all of the feeding compositions in the regimen include colostrum and/or milk replacer. The first feeding composition can also include the pathogen specific avian antibodies against pathogens causing non-digestive tract infections, e.g. distal site infections. The subsequent feeding compositions may also include the pathogen specific avian antibodies. In one preferred embodiment, at least one to three subsequent feeding compositions include the pathogen specific avian antibodies.

Feeding compositions administered to the animal within the first 48 hours after birth include the pathogen specific avian antibodies against pathogens causing non-digestive tract infections, e.g. distal site infections. Preferably, feeding compositions administered to the animal within the first 24 hours include pathogen specific avian antibodies against pathogens causing non-digestive tract infections, e.g. distal site infections. Pathogen specific avian antibodies against pathogens in the digestive tract may also be included in the first and subsequent feeding compositions of the regimen. In some exemplary embodiments, the first feeding composition and the one or more subsequent feeding compositions administered within the first 24 or 48 hours include pathogen specific avian antibodies against pathogens in the digestive tract and against pathogens in distal sites.

Furthermore, pathogen specific avian antibodies against pathogens in the digestive tract may be administered in feeding compositions until the animals develop their own immunity which can take up to several weeks. Feeding compositions administered to the animals after the first 48 hours may not necessarily include pathogen specific avian antibodies against pathogens in distal sites as the avian antibodies can no longer cross the gastric barrier and enter the serum to inactivate the pathogens.

The amount of pathogen specific avian antibodies in the feeding compositions can be, for example, between about 5 grams per quart of feeding composition and about 60 grams per quart of feeding composition. In some exemplary embodiments, the amount of pathogen specific avian antibodies can be between about 10 grams per quart of feeding composition and about 20 grams per quart of feeding composition.

The pathogen specific avian antibodies in the feeding composition can be against one pathogen. Alternatively, the pathogen specific avian antibodies in the feeding composition can be against about two to about four pathogens. Pathogen specific avian antibodies in the feeding composition against more than four pathogens are also within the scope of this disclosure.

Each feeding composition may include about 5 quarts or less of colostrum and/or milk replacer. In exemplary embodiments, each feeding composition can include between about 2 quarts and about 4 quarts of colostrum and/or milk replacer. Amounts greater than 5 quarts area also within the scope of the present disclosure. Animals may be fed about 4 feedings or less per day. In exemplary embodiments, animals can be fed between about 2 to about 3 feedings per day.

The first feeding composition preferably includes at least some pathogen specific avian antibody in colostrum and/or milk replacer. The first feeding composition can include, for example, between about 5 grams and about 60 grams of pathogen specific avian antibodies. In a preferred embodiment, the first feeding composition can include between about 10 grams and about 50 grams of the pathogen specific avian antibodies.

The amount of avian antibodies in the subsequent feeding compositions can vary and can be between about 5 grams and about 60 grams of avian antibodies. In some embodiments, the subsequent feeding composition can include between about 10 grams and about 50 grams of the avian antibodies. Alternatively, in some embodiments, the subsequent feeding compositions (after the first feeding composition) do not include any pathogen specific avian antibodies. In other words, all the desired amount of pathogen specific avian antibody is included in the first feeding composition.

The total amount of pathogen specific avian antibodies administered to the neonatal animal are preferably administered in feeding compositions prior to the cessation of the avian antibodies' ability to cross the digestive tract barrier and enter into the serum of the neonatal animal. The pathogen specific avian antibodies can be included in feeding compositions that are administered to the neonatal animals within the first 48 hours after birth. In some embodiments, the pathogen specific avian antibodies are included in feeding composition that are administered to the neonatal animals within the first 24 hours after birth. In other embodiments, the avian antibodies are included in feeding compositions that are administered to the neonatal animals within the first 12 hours after birth. Embodiments where the total amount of avian antibody is included in the first feeding composition are also within the scope of this invention.

The total amount of pathogen specific avian antibodies administered to the neonatal animal can vary and can be, for example, between about 5 grams and about 250 grams of avian antibodies. In some embodiments, the total amount of pathogen specific avian antibodies administered to the neonatal animal can be between about 10 grams and about 100 grams. In other embodiments, the amount of pathogen specific avian antibodies administered to the neonatal animal can be between about 20 grams and about 60 grams.

The feeding composition may include other components, for example, exogenously added additional protein, other mammalian protein, non-avian antibodies, non-pathogen specific avian antibodies, medium chain fatty acids such as coconut oil and combinations thereof.

The present disclosure also includes methods of feeding neonatal animals. The method includes a feeding regimen of administering one or more feeding compositions that include pathogen specific avian antibodies. Preferably, the first feeding composition administered to the neonatal animal after birth includes the pathogen specific avian antibodies. The first feeding composition preferably includes colostrum from the dam. The amount of pathogen specific avian antibodies administered in the first feeding composition can vary. In some embodiments, the first feeding composition administered to the neonate can include between about 5 grams and about 60 grams of the pathogen specific avian antibodies.

The method can also include one or more subsequent feeding compositions that also include the pathogen specific avian antibodies. In some embodiments, feeding compositions administered during the first 24-48 hours after birth include the pathogen specific avian antibodies. In other words, if the neonate is administered, for example, 3 subsequent feeding compositions within the first 24 hours, i.e. in addition to the first feeding composition, then the 1, 2, or all 3 of these subsequent feeding compositions may include the pathogen specific avian antibodies.

In other embodiments, feeding compositions administered during the first 24-48 hours after birth include the pathogen specific avian antibodies. Feeding compositions with pathogen specific avian antibodies may be administered after the first 48 hours after birth but these avian antibodies, in some embodiments, may not lend any additional protection for pathogenic infections in distal sites, i.e. other than gastric infections.

The method also includes administering a desired amount of total pathogen specific avian antibodies prior to the closure of the gut lining such that avian antibodies can enter the serum of the neonatal animal. In some embodiments, the method includes administering a total of about 250 grams of pathogen specific avian antibodies or less prior to closure of the gut lining. In other embodiments, the method includes administered a total of about 100 grams of pathogen specific avian antibodies or less prior to closure of the gut lining.

The methods can further include detecting the presence of IgY in the serum of the neonatal animal. Administering the feeding compositions with the pathogen specific avian antibodies can result in the presence of IgY in the serum of the neonatal animal. The IgY is derived from the added avian antibodies since mammals do not inherently possess IgY antibodies. The amount of IgY in the serum can be sufficient to neutralize pathogens in the neonatal animals. Neutralization of the pathogens may occur in the bloodstream at sites in the animal aside for the gastrointestinal system. Pathogens that lead to respiratory infections, naval infections, kidney infections and the like may be neutralized at the site of infections. Other types of pathogens may also be neutralized and are all within the scope of this disclosure.

The IgY from the avian antibodies can be detected in the serum of the neonate within about 48 hours after birth. In some embodiments, the IgY derived from the avian antibodies can be detected in the serum of the neonate within about 24 hours after birth. In other embodiments, the IgY derived from the avian antibodies can be detected in the serum of the neonate within about 12 hours after birth.

The IgY can be detected in the serum of the neonate for at least about 48 hours after birth. In some embodiments, the IgY can be detected in the serum of the neonate for at least about 120 hours after birth. Detection of IgY in the serum of the neonate for more than about 120 hours is also within the scope of this disclosure.

Preferably, the amount of pathogen specific avian antibodies administered to the neonate is sufficient for detection of IgY in the serum of the neonate. Detection of the IgY in the serum is known in the art. The amount of IgY detected in the serum of the neonate can vary. In some embodiments, the amount of IgY detected in the serum of neonate is at least about 0.5 ug/ml. The amount of IgY detected in the serum of the neonate can be between about 0.5 ug/ml and about 2.0 ug/ml. Amounts of IgY in the serum of more than about 2.0 ug/ml is also within the scope of this disclosure.

The compositions and methods disclosed herein are particularly useful for pathogenic infections in facilities housing multiple animals or large numbers of animals such as a ranch, farm and the like. Pathogen specific avian antibodies can be isolated for the specific pathogen or pathogens that are prevalent in the herd or farm that the neonate may be exposed to including respiratory, naval, kidney infections. These pathogen specific avian antibodies are administered to the neonates starting with the first feeding composition. Surprisingly, the administration of these avian antibodies can protect the avian animal through the neonatal phase, i.e. until their own immune system is developed, when the pathogen specific avian antibodies are administered within the first 24-48 hours after birth. Continued administration of the pathogen specific avian antibodies against pathogenic infections in distal sites after about the first 24-48 may not be necessary and in fact, can be eliminated to reduce costs while still protecting the neonates from the prevalent pathogenic infections. Avian antibodies, pathogen specific or non-pathogen specific avian antibodies, may be administered to increase the protein content of the composition administered to the neonate.

EXAMPLES

Example 1

This example relates to the use of pathogen specific avian antibodies against bovine coronavirus. The avian antibodies were derived from hens that were hyperimmunized with bovine coronavirus and prepared as described, for example, in U.S. patent application Ser. No. 13/785,838 incorporated herein by reference.

Table 1 shows the use of avian egg powder containing IgY in colostrum of 9 calves. The calves were all under 12 hours of age. They received 10 grams of IgY powder per 1 quart of pasteurized colostrum. Each received 2 quarts or 20 grams of IgY powder. The calves were bled pre-colostrum and then 48 hours later. The sera was prepared and tested via an ELISA test format for the presence of IgY using a kit purchased from ALPCO located in Salem, N.H.

The same serum was also tested in cell culture/virus neutralization assay using MDBK cells and a bovine coronavirus control as shown in Table 2. The presence of the neutralizing antibody to this specific virus was detected after 48 hours in the calf. NOTE: the virus used was an isolate from the same calf operation by Camas, Inc. The IgY product used in the first trial did not contain antibodies derived from the use of this particular isolate but rather from a different source. Thus, this was not a homologous challenge for the test.

TABLE 1

|  |  | 0 hours |  |  | 48 hours |  |
|---|---|---|---|---|---|---|
| Name | Well | 450 | Concentration ng/ml | Well | 450 | Concentration ng/ml |
| Blank | A1 | 0.052 | <6.25 | A5 | 1.466 | 333.78 |
|  | A2 | 0.05 |  | A6 | 1.507 |  |
| R2051 | A3 | 0.051 | <6.25 | B5 | 2.127 | 972.95 |
|  | A4 | 0.057 |  | B6 | 2.009 |  |
| 72869 | B3 | 0.051 | <6.25 | C5 | 2.03 | 204.40 |
|  | B4 | 0.07 |  | C6 | 1.976 |  |
| 72876 | C3 | 0.052 | <6.25 | D5 | 2.073 | 845.41 |
|  | C4 | 0.105 |  | D6 | 1.95 |  |
| 72875 | D3 | 0.051 | <6.25 | E5 | 0.134 | 6.68 |
|  | D4 | 0.053 |  | E6 | 0.136 |  |
| 72867 | E3 | 0.051 | <6.25 | F5 | 2.132 | 1111.76 |
|  | E4 | 0.053 |  | F6 | 2.118 |  |
| 72870 | F3 | 0.05 | <6.25 | G5 | 2 | 703.90 |
|  | F4 | 0.05 |  | G6 | 1.852 |  |
| 72872 | G3 | 0.059 | <6.25 | H5 | 1.867 | 562.33 |
|  | G4 | 0.072 |  | H6 | 1.759 |  |
| 72871 | H3 | 0.059 | <6.25 | A7 | 1.949 | 659.68 |
|  | H4 | 0.055 |  | A8 | 1.847 |  |

TABLE 2

Bovine Coronavirus Serum Neutralization

| Calf number | Age | Antibody titer |
|---|---|---|
| R2051 | 0 hr | 0 |
|  | 48 hr | 0 |
| 72869 | 0 hr | 0 |
|  | 48 hr | 4 |
| 72876 | 0 hr | 0 |
|  | 48 hr | 4 |
| 72875 | 0 hr | 0 |
|  | 48 hr | 4 |
| 72867 | 0 hr | 0 |
|  | 48 hr | 8 |
| 72870 | 0 hr | 0 |
|  | 48 hr | 32 |
| 72872 | 0 hr | 0 |
|  | 48 hr | 16 |
| 72871 | 0 hr | 0 |
|  | 48 hr | 0 |
| 72874 | 0 hr | Not done due to lack of serum |

Example 2

Table 3 shows the results from another trial comparing the use of just colostrum or colostrum with 10 gm/qt of pathogen specific avian antibodies and administered to the neonate. These calves were all fed pathogen specific avian antibodies with colostrum within 6 hours of delivery. Each was given 4 qts of colostrum with or without IgY as noted. They were bled at 0, 48 and 120 hours to determine if IgY antibodies can be detected within the calves.

Table 4 shows the cell culture/virus neutralization results from this sera. The presence of coronavirus neutralizing antibodies was detected up to 120 hours post-parturition in calves. The antibody product delivered in colostrum to the calves was derived from hen eggs where the hen was hyper-immunized from isolates from this particular operation. Thus, this was a homologous challenge.

TABLE 3

IgY Data IgY Values

| Ear Tag | Breed | Colostrum Time | Avian Antibodies (y/n) | IgY serum Concentration | | |
|---|---|---|---|---|---|---|
| | | | | Initial (μg/ml) | 48 Hours μg/ml | 5 days μg/ml |
| 75482 | Holstein | 9am | yes | <0.01 | | |
| 75483 | Jersey/Angus | | yes | <0.01 | | |
| 75484 | Holstein | 9:30am | no | <0.01 | <0.01 | <0.01 |
| 75485 | Holstein | | no | <0.01 | <0.01 | <0.01 |
| 75486 | Jersey/Angus | 12pm | yes | <001 | 1.46 | 0.65 |
| 75487 | Jersey | | yes | <0.01 | No data | 0.66 |
| 75488 | Jersey | | no | <0.01 | <0.01 | <0.01 |
| 75489 | Holstein | | no | <0.01 | <0.01 | <0.01 |
| 75490 | Jersey | 2pm | no | <0.01 | <0.01 | <0.01 |
| 75491 | Holstein | 12:40pm | yes | <0.01 | 2.59 | 0.8 |
| 75492 | Jersey | | yes | <0.01 | 2.61 | 1.2 |
| 75493 | Grey (Holstein) | | yes | <0.01 | 1.12 | 0.61 |
| 75494 | Jersey | | yes | <0.01 | 1.28 | 0.78 |
| 75495 | Jersey | | yes | <0.01 | 1.42 | 0.95 |
| 75496 | Jersey | 1:30pm | no | <0.01 | <0.01 | <0.01 |
| 75497 | Jersey | | yes | <0.01 | 1.77 | 1.45 |
| 75498 | Angus/Jersey | 2pm | no | <0.01 | <0.01 | No Data |
| 75499 | Jersey | | no | <0.01 | <0.01 | <0.01 |
| 75500 | Jersey | 2:30pm | no | <0.01 | <0.01 | <0.01 |
| 75501 | Jersey | | no | <0.01 | <0.01 | <0.01 |

TABLE 4

Coronavirus serum neutralization Assay

| Animal # | Treatment | 0 hr | 48 hr | 120 hr |
|---|---|---|---|---|
| 75484 | no | 0 | | 0 |
| 75485 | no | 0 | 0 | 0 |
| 75488 | no | 0 | 0 | 0 |
| 75489 | no | 0 | 0 | 0 |
| 75490 | no | 0 | 16 | 16 |
| 75496 | no | 0 | 0 | 0 |
| 75498 | no | 0 | 0 | 0 |
| 75499 | no | 0 | 0 | 0 |
| 75500 | no | 0 | 0 | 0 |
| 75501 | no | 0 | 0 | 0 |
| 75482 | yes | 0 | 16 | 32 |
| 75483 | yes | 0 | 16 | 64 |
| 75486 | yes | 0 | 16 | 0 |
| 75487 | yes | 0 | 0 | 0 |
| 75491 | yes | 0 | 128 | 64 |
| 75492 | yes | 0 | 64 | 64 |
| 75493 | yes | 0 nd | | |
| 75494 | yes | 0 nd | | |
| 75495 | yes | 0 nd | | |
| 75497 | yes | 0 nd | | |

The desired total protein level (including immunoglobulins) in the bovine is Total Protein (TP) #5.4 via a refractometer reading.

Although the present invention has been described with reference to preferred embodiments, workers skilled in the art will recognize that changes may be made in form and detail without departing from the spirit and scope of the invention.

What is claimed is:

1. Feeding compositions for neonatal ruminant animals comprising:
   one or more birth to 24-48 hour feeding compositions comprising colostrum and/or milk replacer; and pathogen specific avian IgY antibodies against at least one pathogen, and
   one or more after 24-48 hour feeding compositions comprising colostrum and/or milk replacer, wherein the after 24-48 hour feeding compositions do not include the pathogen specific avian IgY antibodies;
   wherein the pathogen causes an infection in a neonatal animal at a site outside of the digestive tract of the neonatal animal and the feeding compositions protect the neonatal animal against infections outside of the digestive tract,
   wherein the concentration of the avian IgY antibodies in the one or more birth to 24-48 hour feeding compositions is sufficient for crossing the digestive tract barrier and detection of the avian IgY antibodies in the serum of the neonatal animal,
   wherein the neonatal animal is a ruminant,
   wherein the pathogen is bovine coronavirus, and
   wherein the infection is a respiratory infection, a lung infection or combinations thereof.

2. The compositions of claim 1, wherein the one or more of the birth to 24-48 hour feeding compositions comprises between about 5 grams and about 60 grams of the avian IgY antibodies.

3. The compositions of claim 1, wherein the one or more of the birth to 24-48 hour compositions comprises between about 5 grams per quart and about 20 grams per quart of the avian IgY antibodies.

4. The compositions of claim 1, wherein the compositions are free of dried colostrum powder.

5. A neonatal animal feeding regimen comprising:
   two or more feeding compositions, the two or more feeding compositions comprising
   one or more birth to 24-48 hour feeding compositions comprising colostrum and/or milk replacer and pathogen specific avian IgY antibodies specific against at least one pathogen; and one or more after 24-48 hour feeding compositions comprising colostrum and/or milk, wherein the after 24-48 hour feeding compositions do not include the pathogen specific avian IgY antibodies;
   wherein the pathogen causes an infection in the neonatal animal at a site outside of the digestive tract of the animal and the feeding regimen protects the neonatal animal against the infection outside of the digestive tract;
   wherein the concentration of the avian IgY antibodies in the one or more birth to 24-48 hour feeding compositions is sufficient for crossing the digestive tract barrier and detection of the avian IgY antibodies in the serum of the neonatal animal,
   wherein the regimen comprises feeding a first feeding of the birth to 24-48 hour composition within 12 hours of birth of the neonatal animal, wherein the neonatal animal is a ruminant, wherein the pathogen is bovine coronavirus, and
   wherein the infection is a respiratory infection, a lung infection or combinations thereof.

6. The feeding regimen of claim 5, wherein the amount of the pathogen specific avian IgY antibodies administered in the birth to 24-48 hour feeding compositions is between about 5 grams and 250 grams and wherein the total amount of the pathogen specific avian IgY antibodies administered in the regimen is less than about 250 grams.

7. The feeding regimen of claim 5, wherein the first birth to 24-48 hour feeding composition comprises the total amount of the pathogen specific avian IgY antibody.

8. The feeding regimen of claim 5, wherein the amount of the pathogen specific avian IgY antibodies in the first birth to 24-48 hour feeding composition is between about 10 grams and about 60 grams.

9. The feeding regimen of claim 5, wherein the regimen further comprises one or more subsequent birth to 24-48 hour feeding compositions after the first birth to 24-48 hour feeding composition, wherein the one or more subsequent birth to 24-48 hour feeding compositions comprise pathogen specific avian IgY antibodies, wherein the subsequent birth to 24-48 hour feeding compositions are administered within 24 hours of birth.

10. The feeding regimen of claim 9, wherein the first birth to 24-48 hour feeding composition comprises between about 10 grams and about 60 grams of the avian IgY antibodies and the one or more subsequent birth to 24-48 hour feeding compositions comprise between about 10 grams and about 120 grams of the total avian IgY antibodies, when the subsequent birth to 24-48 hour feeding compositions are for administration within 24 hours of birth.

\* \* \* \* \*